United States Patent [19]

Muz

[11] Patent Number: 5,054,488

[45] Date of Patent: Oct. 8, 1991

[54] OPTOELECTRONIC SENSOR FOR PRODUCING ELECTRICAL SIGNALS REPRESENTATIVE OF PHYSIOLOGICAL VALUES

[75] Inventor: Edwin Muz, Reutlingen, Fed. Rep. of Germany

[73] Assignee: Nicolay GmbH, Kirchhein/Teck, Fed. Rep. of Germany

[21] Appl. No.: 498,750

[22] Filed: Mar. 26, 1990

[30] Foreign Application Priority Data

Apr. 20, 1989 [DE] Fed. Rep. of Germany ....... 3912993

[51] Int. Cl.$^5$ ................................................. A61B 5/00
[52] U.S. Cl. ..................................... 128/633; 128/665
[58] Field of Search ................. 128/633, 634, 665, 666

[56] References Cited

U.S. PATENT DOCUMENTS

| 4,041,932 | 8/1977 | Fostick | 128/633 |
| 4,825,879 | 5/1989 | Tan et al. | 128/633 |
| 4,830,014 | 5/1989 | Goodman | 128/665 |
| 4,865,038 | 9/1989 | Rich et al. | 128/633 |
| 4,964,408 | 10/1990 | Hiah et al. | 128/633 |
| 4,974,591 | 12/1990 | Awazu et al. | 128/633 |

FOREIGN PATENT DOCUMENTS 0127947  3/1984  European Pat. Off. .

Primary Examiner—William E. Kamm
Assistant Examiner—Scott N. Akers
Attorney, Agent, or Firm—Roylance, Abrams, Berdo & Goodman

[57] ABSTRACT

An optoelectronic sensor produces electrical signals representative of measurements of physiological values, especially the circulation parameters of a person. The sensor has at least one radiation transmitter and at least one receiver for radiation influenced by the physiological values being measured. The transmitter and receiver are covered with a transparent adhesive layer on their sides turned toward the object to be measured. The layer is transparent and adhesive at least on its side turned toward to the object to be measured. This transparent layer engages directly on the radiation outlet surface of the radiation transmitter and the radiation admission surface of the radiation receiver.

9 Claims, 2 Drawing Sheets

OPTOELECTRONIC SENSOR FOR PRODUCING ELECTRICAL SIGNALS REPRESENTATIVE OF PHYSIOLOGICAL VALUES

REFERENCE TO RELATED APPLICATION

This application is related to U.S. patent application Ser. No. 07/324,454, filed Mar. 16, 1989 and entitled Sensor For Measuring Pulse Rate and/or Oxygen Saturation of Blood and Process for Making Same, the subject matter of which is hereby incorporated by references.

FIELD OF THE INVENTION

The present invention relates to an optoelectronic sensor for producing electrical signals for measuring physiological values, especially the circulation parameters of a person.

BACKGROUND OF THE INVENTION

The fastening of transmitters and receivers of optoelectronic physiological sensors onto the skin surface is very problematical. Even the slightest movements of the parts of the sensor relative to the skin surface lead to numerous artifacts (structures in a fixed cell or tissue formed by manipulations or by the reagent), and thus, lead to signal fluctuations. To avoid these movements, both the transmitter and the receiver need to be tightly pressed onto the skin surface.

Tight pressing can disturb the circulation of the blood through the capillary bed, which disturbance can also lead to erroneous measurements and recordings. A slighter inclination to the formation of artifacts simultaneously with higher signal quality cannot be attained with flexible or resilient clamps on the skin, or by means of elastic strips and the like.

Because of this, it has been suggested (see, e.g., European Patent 0 127 947 A2) to affix a light-impermeable strip to the support layer for the transmitter and receiver. The strip, in the area of the light outlet surface of the transmitter and in the area of the light admission surface of the receiver, has an opening for each. This strip is affixed to a sheet of clear polyester, coated on both sides with an adhesive material. Also, a porous protective layer can be affixed to the reverse side of the light impermeable layer supporting the transmitter and receiver members. Despite this costly construction of the transmitter and of the adhesive connection between the transmitter and the skin surface, the signal quality is still inadequate.

SUMMARY OF THE INVENTION

A object of the present invention is to disclose an optoelectronic sensor for producing electrical signals representative of physiological values which appreciably avoids artifacts and has the capacity to deliver a high quality signal.

The foregoing object is obtained by an optoelectronic sensor for producing electrical signals representative of physiological values, especially human circulation parameters. The sensor comprises a radiation transmitter having a radiation outlet surface, and a radiation receiver sensitive to receiving radiation emitted by the transmitter and influenced by the physiological values. The receiver is coupled to the transmitter and has a radiation admission surface. A transparent adhesive layer covers the transmitter and the receiver on at least sides thereof facing an object to be measured. The adhesive layer directly engages the radiation outlet surface and the radiation admission surface.

In this manner, the transparent adhesive layer, at least on its side turned toward the target or object being measured, also directly engages the area of the radiation outlet surface of the transmitter and the radiation admission surface of the receiver. An optical path (or radiation path) lies between the skin surface on the one hand and the transmitter, as well as the receiver on the other hand. The optical path consists of material of approximately identical optical density.

With the known sensor, on the contrary, incorporation of air is unavoidable, such that the optical path is formed of materials with different optical densities, such optical path has considerable internal reflections causing leakage of the radiation.

In the present invention, an optimum optical coupling between the transmitter, the skin surface and the receiver is guaranteed. The optical path does not lead to formation of internal reflections. A greater portion of the radiation thus pervades the tissue, whereupon the portion of radiation reaching the receiver is also considerably greater, attaining an excellent quality signal.

The inclination to form artifacts can also be suppressed for the most part by virtue of the adhering layer. In one preferred embodiment, the transparent layer has a highly transparent gel of silicon base. This material provides good optical qualities and good adhesion, and thus, fulfills all the requirements. Such gel may be obtained from Wacker-Chemie GmbH, Munich, West Germany, under the name RTV-2 Silikonkautschuk VP 7612, as a two-component sealing compound.

The adhesiveness of the gel is preferably adjusted to the desired value corresponding to the purpose of its use. The adhesiveness is adjusted by varying the mixture ratios of the two components forming the gel.

The transparent layer directly engaging the radiation outlet surface of the transmitter and the radiation admission surface of the receiver can be provided on one side of a transparent support sheet. The other side of the support sheet is provided with a transparent layer consisting of the same material. Such support sheet can also provide additional electrical insulation. However, it is especially advantageous for such support sheet to be coated on both sides for the formation of adhesive laminae. The lamina dimensions can be coordinated with the dimensions of the transmitter and those of the receiver. The adhesive lamina can be applied on each or a common adhesive lamina can be applied to both of the transmitter and receiver. After measurement, the lamina can be removed and discarded for reasons of hygiene. Such adhesive laminae can also have an uncoated gripping strap to facilitate handling.

The sensor can be covered on all sides with the layer of gel at least in the area of application. Thus, the properties of the gel can be selected to electrically insulate the transmitter and the receiver from the skin as well as to seal the transmitter and receiver from water, moisture and perspiration.

Insofar as required, on the side of the sensor which is turned away form the target to be measured, the gel layer can be covered with a reflective layer.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure.

DETAILED DESCRIPTION OF THE INVENTION

Figure 1:
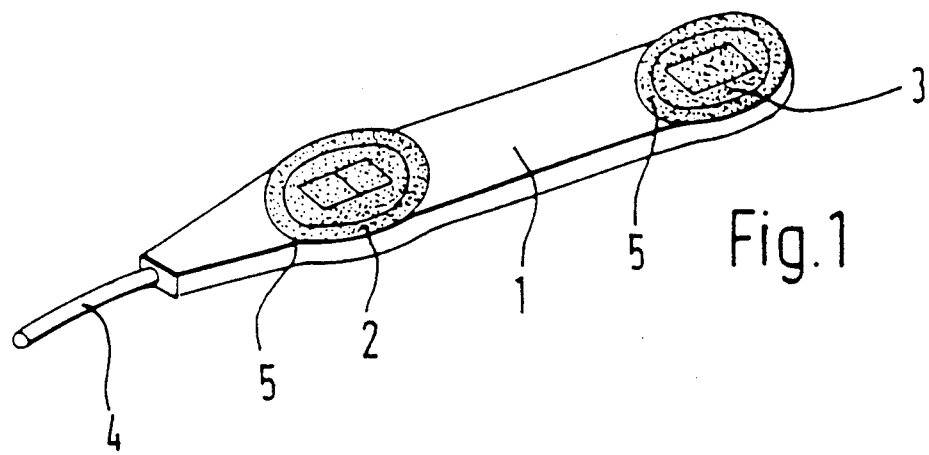
FIG. 1 is a perspective view of an optoelectronic sensor according to a first embodiment of the present invention with gel only in the transmitter and receiver areas.

An optoelectronic sensor produces electrical signals representative of physiological values. The sensor can be used, for instance, for oximetry (the measure of the degree of oxygen saturation of blood) and plethysmography (the measure of the changes in the size of a part of the body by measuring changes in the amount of blood in that part).

The optoelectronical sensor of the present invention has a strip-like, flexible base member 1 made of a flexible synthetic resin, for instance, silicon rubber. A radiation transmitter 2 and a radiation receiver 3 are embedded in this strip-like base member 1, at some distance from each other along its length. The transmitter light discharge surface and the receiver light admission surface are independent of each other and unconfined. Radiation transmitter 2 and radiation receiver 3 are soldered onto a not shown, flexible conductor plate. One end of the conductor plate is soldered to a connection cable 4. The distance between radiation transmitter 2 and radiation receiver 3 is selected so that radiation transmitter 2 and radiation receiver 3 can be arranged on opposite sides of the fingers of a person.

The radiation outlet surface of radiation transmitter 2 and the radiation admission surface of receiver 3, as well as border area of base member 1 surrounding the transmitter and receiver, are coated with a highly transparent, adhesive gel 5. For the first exemplary embodiment, gel 5 is of the type distributed by Wacker-Chemie GmbH, Munich, West Germany, under the name RTV-2 Silikonkautschuk VP 7612, which is a mixture of two components applied to the surfaces to be coated. The mixing ratio of the two components influences the adhesiveness. After a vulcanization period, dependent upon the vulcanization temperature, the properties of gel 5 no longer change.

For execution of the measurement, gel 5 covering radiation transmitter 2 makes contact with the measurement area of the skin surface, and produces a reliable adhesive connection, essentially suppressing the formation of artifacts. Correspondingly, radiation receiver 3 is affixed to the associated measurement surface. The radiation emanating from radiation transmitter 2 must penetrate gel 5 only until it reaches the skin surface, and then pervades or soaks into the skin. The radiation emanating from the body part, influenced by the physiological value being measured, must pervade only gel 5 again as it comes out of the body, before reaching the radiation admission surface of radiation receiver 3. Thus, an optimum optical coupling of radiation transmitter 2 and radiation receiver 3 with the target, the object to be measured, is obtained. Additionally, an excellent quality signal is obtained.

Figure 2:
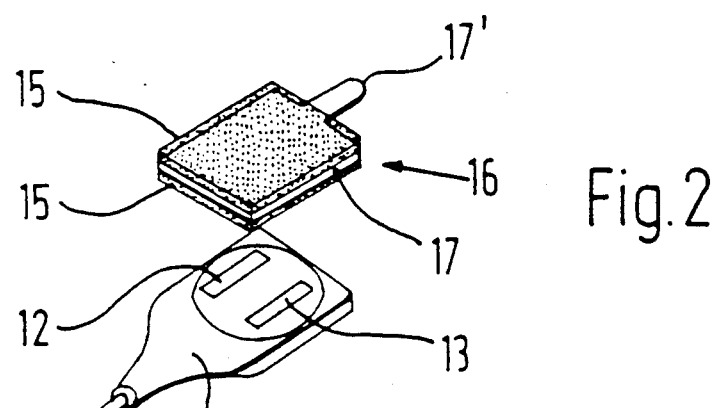
FIG. 2 is a perspective view of an optoelectronic sensor according to a second embodiment of the present invention operated by reflection with a raised adhesive lamina.

In the optoelectronic sensor shown in FIG. 2, the radiation transmitter 12 and the radiation receiver 13 are arranged at a relatively small distance from each other, one adjacent to the other on a not shown conductor plate which is probably quadratic. The conductor plate is soldered to a connection cable 14. The base member 11, in which the conductor plate, radiation transmitter 12 and radiation receiver 13 are embedded, with the exception of the radiation outlet surface and the radiation admission surface is silicon rubber, as in the first exemplary embodiment. However, the base member could also be of some other synthetic resin material, because in this embodiment the flexibility does not play an essential role. This exemplary embodiment actually works on a reflective basis. In other words, the radiation emanating from the radiation transmitter 12 is reflected by the object to be measured, so that only reflected radiation reaches radiation receiver 13.

An adhesive lamina, indicated in its entirety as 16, reliably connects the sensor and the object to the measured, i.e., the skin surface of a person. For an optimum optical coupling, adhesive lamina 16 has a highly transparent support sheet 17. The support sheet dimensions are coordinated approximately with the dimensions of the front surface of the sensor. This support sheet 17 has a gripping strap 17' on one side. Both sides of support sheet 17, with the exception of its gripping strap 17', are coated with a highly transparent, adhesive gel 15. The gel is composed of the same material as gel 5 of the first exemplary embodiment. The adherence between gel 15 and support sheet 17 is greater than between gel 15 and the front side of the sensor.

For a measurement, adhesive lamina 16 is applied on the front of the sensor. The side of adhesive lamina 16, not facing or remote from sensor front side, is then installed on the measurement surface of the object to be measured. Of course, it is also possible to first install the adhesive lamina 16 on the measuring point and thereafter to initiate the use of the sensor. Also, in this case, a good adhesive connection for the most part suppresses the formation of artifacts and provides an optimum optical coupling. Support sheet 17 has an optical density at least nearly identical to the optical density of gel 15, and can improve the electrical insulation of radiation transmitter 12 and radiation receiver 13 relative to the skin surface of the person being tested.

Figure 3:
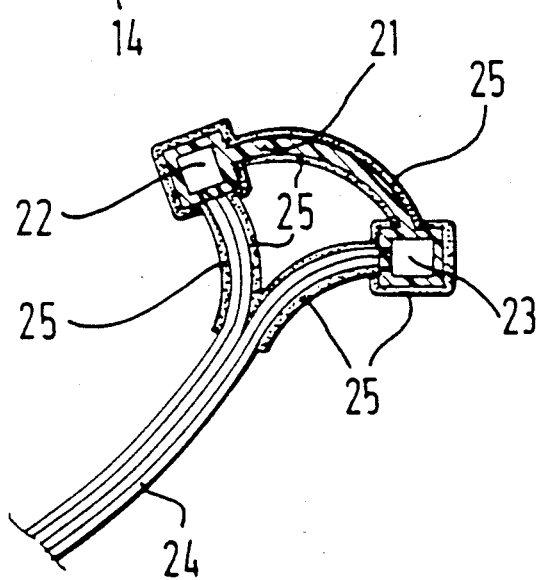
FIG. 3 is a side elevational view in section of an optoelectronic sensor according to a third embodiment of the present invention for fastening to a nose.

The exemplary embodiment shown in FIG. 3 is intended for installation on the nose of a person. One end of a four-polar connection cable 24 is subdivided in its middle and is spread apart in a Y shape. The one pair of conductors is soldered onto radiation transmitter 22, while the other pair is soldered onto radiation receiver 23. Radiation transmitter 22 and radiation receiver 23 are embedded in opposite end segments of a base member 21 of silicon rubber, while the radiation outlet surface and the radiation admission surface are left uncovered. The notably narrower, flexible middle segment of the base member has the shape of a curve segment. In all, the sensor has the inner and outer contour of a sector of a circle.

The sensor is coated with gel 25 in the entire application area, i.e., in the total area of base member 21 and the subdivided cable end. For this purpose, the entire sensor, inclusive of the separated end parts of the connection cable, is immersed in gel 25. This gel 25 is of the same material used for gel 5 of the first exemplary embodiment.

Figure 4:
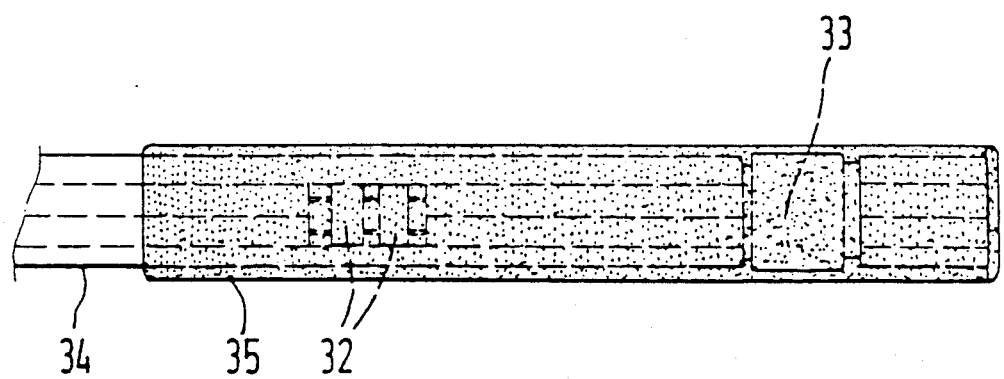
FIG. 4 is a plan view of an optoelectronic sensor according to a fourth embodiment of the present invention.
Figure 5:
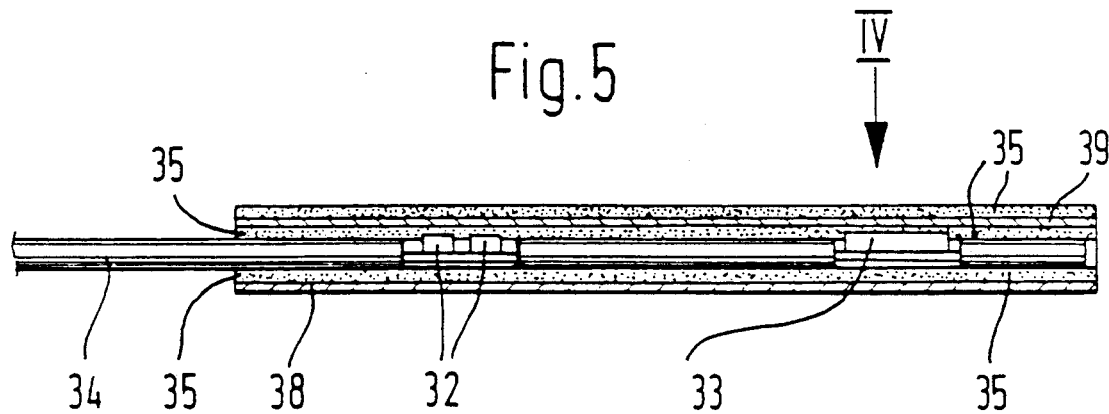
FIG. 5 is a side elevational view in section of the optoelectronic sensor of FIG. 4.

In the exemplary embodiment shown in FIGS. 4 and 5, the sensor has a four-polar flat cable 34. Two radiation transmitters 32 are directly soldered onto cable 34 adjacent to one other along the cable length. Also along the cable length, at considerable spacing from these transmitters, radiation receiver 33 is located. The end segment of flat cable 34 supporting these optical structural components is coated with a gel 35, applied by immersion. On the reverse side of the end segment of flat cable 34 coated with gel 35, a sheet of paper 38 coated with aluminum is applied, and is held tightly thereon by gel 35. The aluminum coating serves as reflector and as a shield. On the front side, opposite paper 38, transparent sheet 39 is applied and is coated with gel 35 on the side not adjacent to or remote from the flat cable. Sheet 39 serves as additional insulation for the skin surface. Since sheet 39 has the identical optical density as gel 35, no inner reflections originate therein.

While various embodiments have been chosen to illustrate the invention, it will be understood by those skilled in the art that various changes and modifications can be made therein without departing from the scope of the invention as defined in the appended claims.

What is claimed is:

1. An optoelectronic sensor for producing electrical signals representative of physiological values, especially human circulation parameters, comprising:
    a radiation transmitter having a radiation outlet surface;
    a radiation receiver sensitive to receiving radiation emitted by said transmitter and influenced by the physiological values, said receiver having a radiation admission surface; and
    a transparent adhesive layer covering said transmitter and said receiver on at least sides thereof facing an object to be measured, said adhesive layer directly engaging said radiation outlet surface and said radiation admission surface.

2. An optoelectronic sensor according to claim 1 wherein said transparent adhesive layer comprises a transparent gel of a silicon base.

3. An optoelectronic sensor according to claim 2 wherein said gel comprises first and second components mixed in a ratio.

4. An optoelectronic sensor according to claim 1 wherein said transparent adhesive layer comprises a transparent support sheet bearing transparent adhesive material on both sides of said transparent support sheet.

5. An optoelectronic sensor according to claim 4 wherein said transparent support sheet has a shape corresponding to a surface area of said outlet surface and said admission surface of said transmitter and said receiver, respectively, to be covered thereby.

6. An optoelectronic sensor according to claim 5 wherein said support sheet comprises an uncoated gripping strap.

7. An optoelectronic sensor according to claim 4 wherein said support sheet comprises an uncoated gripping strap.

8. An optoelectronic sensor according to claim 1 wherein said transparent layer comprises a transparent adhesive gel layer on all sides of an area of application of the sensor.

9. An optoelectronic sensor according to claim 8 wherein said gel layer is covered with a reflecting layer on a side of said gel layer remote from the object to be measured.

* * * * *